(12) United States Patent
Iyer et al.

(10) Patent No.: US 9,345,895 B2
(45) Date of Patent: May 24, 2016

(54) IMPLANTABLE MEDICAL DEVICE AND FEEDTHROUGH AND METHOD OF MAKING SAME

(71) Applicant: MEDTRONIC, INC., Minneapolis, MN (US)

(72) Inventors: Rajesh V. Iyer, Eden Prairie, MN (US); Michael G. Marinkov, Woodbury, MN (US); Lea A. Nygren, Bloomington, MN (US); Brad C. Tischendorf, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 307 days.

(21) Appl. No.: 13/772,490

(22) Filed: Feb. 21, 2013

(65) Prior Publication Data

US 2013/0289681 A1 Oct. 31, 2013

Related U.S. Application Data

(60) Provisional application No. 61/638,759, filed on Apr. 26, 2012.

(51) Int. Cl.
*A61N 1/00* (2006.01)
*A61N 1/375* (2006.01)
*B23K 35/02* (2006.01)

(52) U.S. Cl.
CPC .......... *A61N 1/3754* (2013.01); *B23K 35/0244* (2013.01); *Y10T 29/49222* (2015.01)

(58) Field of Classification Search
CPC ............. A61N 1/3754; B23K 35/0244; Y10T 29/49222
See application file for complete search history.

(56) References Cited

U.S. PATENT DOCUMENTS

| 4,225,262 | A  | * | 9/1980 | Koop et al. ................ 403/272 |
| 6,765,780 | B2 | * | 7/2004 | Brendel et al. ............. 361/302 |
| 7,689,288 | B2 |   | 3/2010 | Stevenson et al. |
| 7,765,005 | B2 |   | 7/2010 | Stevenson |
| 2002/0170735 | A1 | * | 11/2002 | Broad et al. ............... 174/84 R |
| 2011/0235239 | A1 |   | 9/2011 | Teske |

OTHER PUBLICATIONS

Iyer et al., "Implantable Medical Device With Feedthrough, Feedthrough and Method", U.S. Appl. No. 13/772,465, filed Feb. 21, 2013, 16 pages.

* cited by examiner

*Primary Examiner* — Niketa Patel
*Assistant Examiner* — Lindsey G Hankins

(57) ABSTRACT

Implantable medical device having a feedthrough, a feedthrough and method for making such feedthrough. The feedthrough has a ferrule, an electrically conductive pin, a preform having a preform liquidus temperature, a capacitor, positioned within the ferrule abutting the preform, having a coating having a coating liquidus temperature and being configured to electrically couple with the preform, and an insulative assembly configured, at least in part, to seal against passage of a liquid through the ferrule, and having an insulative assembly liquidus temperature. The coating liquidus temperature is greater than the preform liquidus temperature and the coating liquidus temperature being greater than the insulative assembly liquidus temperature.

16 Claims, 4 Drawing Sheets

IMPLANTABLE MEDICAL DEVICE AND FEEDTHROUGH AND METHOD OF MAKING SAME

FIELD

The present invention relates generally to an implantable medical device having a feedthrough, a feedthrough and method of making such feedthrough and, more particularly, an implantable medical device having a feedthrough, a feedthrough and method of making such feedthrough with components having particular liquidus temperatures.

BACKGROUND

Implantable medical devices which deliver electrical stimulation to patient tissue, such as pacemakers, defibrillators and neurological stimulators, need to be able to transmit electrical pulses from electronic circuits within the implantable medical device while at the same time inhibiting bodily fluids from entering the implantable medical device and substances from leaving the implantable medical device to the extent possible. Electrical feedthroughs are commonly configured on such implantable medical devices to provide for the transmission of electrical pulses while also maintaining substantial or complete fluid isolation between the interior of the implantable medical device and the patient. Other implantable medical devices may utilize feedthroughs for other purposes providing an electrical ingress or egress to or from the implantable medical device or providing a throughput for some other therapeutic or diagnostic function. In addition, it is sometimes desirable for the feedthrough to contain a capacitor/filter assembly to reduce the amount of electromagnetic interference (EMI) entering the device.

Historically, implantable medical device feedthroughs have utilized a ferrule extending through a housing of the implantable medical device. An electrically conductive wire or pin is positioned within and extending through the ferrule and sealed to provide isolation. Such seals have typically incorporated a sealing member and gold preform rings and solder rings to bond the bulk to the pin and the ferrule.

Traditionally, while the gold has provided bonding while also being substantially biocompatible, the solder provides bonding which is inexpensive and easy to manipulate. In addition, gold and solder have, in the past, each been utilized because each has different bonding properties. While solder may bond easily to many substances, gold may have greater difficulty bonding or be incapable of bonding to certain substances to which solder may bond easily.

As a result of the different thermal properties of the different materials which have been utilized in the construction of feedthroughs, the manufacturing process for feedthroughs has involved a relatively large number of steps in comparison to the number of components. In particular, because the gold and solder have different melting points, each must be heated separately, resulting in twice the heating steps, with the resultant increase in manufacturing time, complexity and cost. Additionally, solder and gold each generally may have a different surface chemistry for bonding due to the large temperature offsets possibly resulting in increased in manufacturing steps.

SUMMARY

An implantable medical device having feedthroughs and a feedthrough have been developed which addresses these challenges by reducing the complexity of the feedthrough by replacing solder components with gold components. The use of gold by itself rather than gold and solder means that a single brazing step may be utilized to secure components in the feedthrough with respect to one another, in contrast to two brazing steps which may be utilized to braze a feedthrough with solder and gold together.

In order to utilize gold to bond certain components rather than solder, such components as capacitors are metalized in ways contrary to many conventional applications. Capacitors have in the past been metalized with silver-palladium to promote bonding with solder, as known in the art. However, silver-palladium deteriorates at temperatures below the melting temperature of gold. Accordingly, capacitors have been developed which are metalized with niobium or other materials with a melting temperature greater than that of the melting temperature of gold and which promote bonding with gold.

In embodiments, an implantable medical device having a feedthrough and a feedthrough has a ferrule, an electrically conductive pin, a preform having a preform liquidus temperature, a capacitor, positioned within the ferrule abutting the preform having a coating, having a coating liquidus temperature and being configured to electrically couple with the preform, and an insulative assembly configured, at least in part, to seal against passage of a liquid through the ferrule, and having an insulative assembly liquidus temperature. The coating liquidus temperature is greater than the preform liquidus temperature and the coating liquidus temperature being greater than the insulative assembly liquidus temperature.

In embodiments, the coating liquidus temperature, the preform liquidus temperature and the insulative assembly liquidus temperature are selected so that the preform, the capacitor, the insulative assembly, the pin and the ferrule are secured with respect to one another with a single step.

In embodiments, the single step comprises an application of heat.

In embodiments, the preform is a first preform comprised of a preform material, the insulative assembly comprises an insulator and a second preform comprised of the preform material having the preform liquidus temperature and configured to secure the insulator with respect to the pin and the ferrule, and the insulative assembly liquidus temperature is equal to the preform liquidus temperature.

In embodiments, the first preform comprises a first inner preform proximate the pin and a first outer preform proximate the ferrule and the second preform comprises a second inner preform proximate the pin and a second outer preform proximate the ferrule.

In embodiments, the preform material is substantially gold and the preform liquidus temperature and the insulative assembly liquidus temperature are a liquidus temperature of gold.

In embodiments, the coating of the capacitor is comprised of niobium.

In embodiments, the insulative assembly and the capacitor form a gap within the ferrule between the insulative assembly and the capacitor.

In embodiments, the gap is at least partially filled with a non-conductive material.

In embodiments, the ferrule forms a hole proximate the gap and the ferrule is configured so that the non-conductive material may be inserted though the hole in the ferrule.

In embodiments, the pin extends longitudinally through the ferrule, the capacitor and the insulative assembly.

In an embodiment, a method of making a feedthrough comprises the steps of extending an electrically conductive pin at least partially through a ferrule, positioning a capacitor within the ferrule, the capacitor having a coating having a coating liquidus temperature, positioning a first preform proximate a first side of the capacitor within the ferrule, the preform having a preform liquidus temperature, positioning an insulative assembly within the ferrule proximate a second side of the capacitor opposite of the first side, the insulative assembly having an insulative assembly liquidus temperature, and applying a temperature at least as high as the preform liquidus temperature and the insulative assembly liquidus temperature but less than the capacitor liquidus temperature, sealing, at least in part, the ferrule from a passage of a liquid through the ferrule. The coating liquidus temperature is greater than the preform liquidus temperature and the coating liquidus temperature being greater than the insulative assembly liquidus temperature.

In an embodiment, the coating liquidus temperature, the preform liquidus temperature and the insulative assembly liquidus temperature are selected so that the preform, the capacitor, the insulative assembly, the pin and the ferrule are secured with respect to one another during the applying a temperature step.

In an embodiment, the preform is a first preform comprised of a preform material, the insulative assembly comprises an insulator and a second preform comprised of the preform material having the preform liquidus temperature, the insulative assembly liquidus temperature being equal to the preform liquidus temperature, and the second preform secures the insulator with respect to the pin and the ferrule during the applying a temperature step.

In an embodiment, the positioning the insulative assembly step and the positioning the capacitor step form a gap within the ferrule between the insulative assembly and the capacitor.

In an embodiment, the method further comprises the step of filling the gap with a non-conductive material.

In an embodiment, the ferrule forms a hole proximate the gap and the filling step is accomplished by inserting the non-conductive material through the hole in the ferrule.

In an embodiment, all of the positioning steps are accomplished so that the pin extends longitudinally through the ferrule, the capacitor and the insulative assembly.

FIGURES

DESCRIPTION

Figure 1:
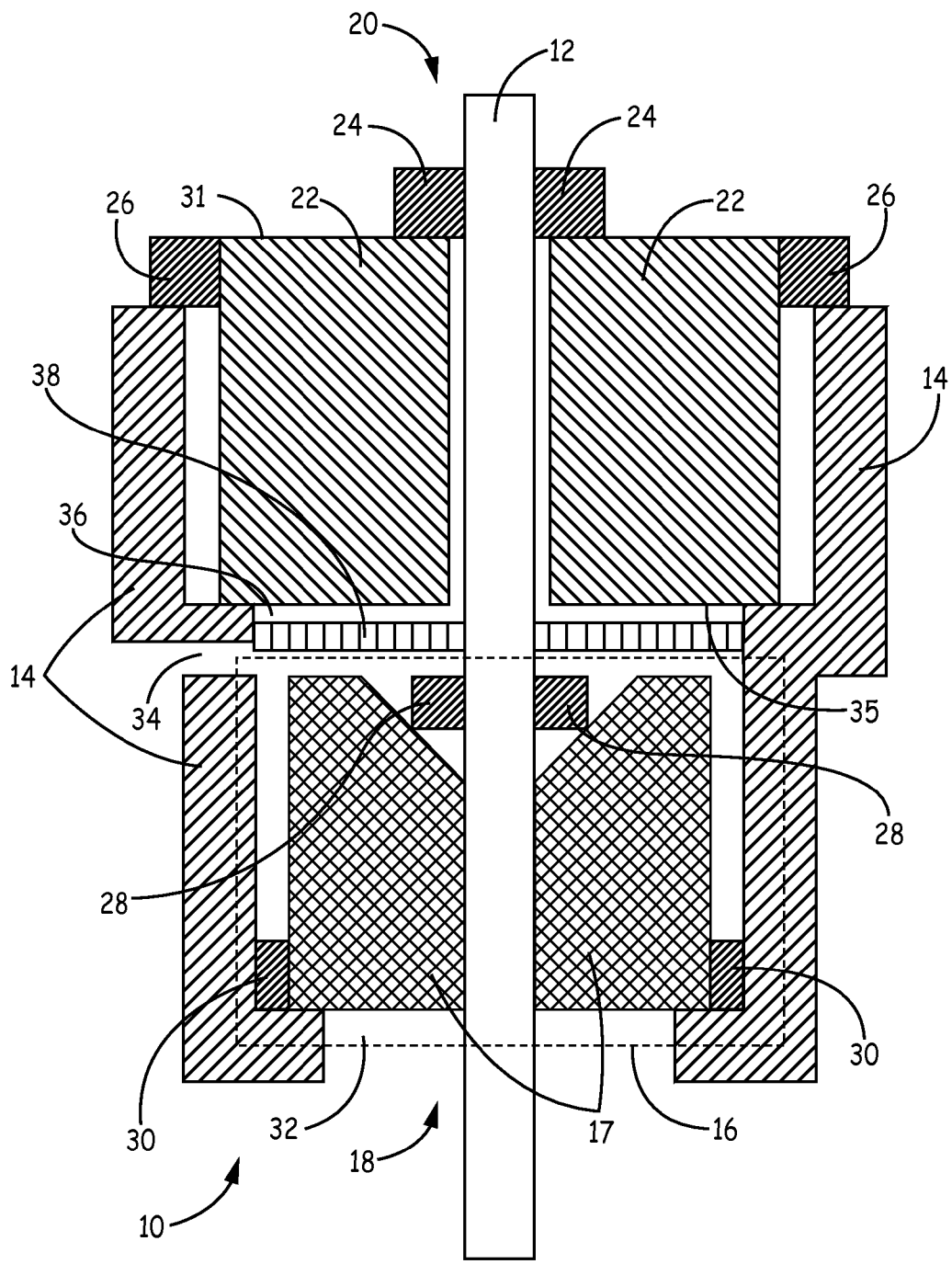
FIG. 1 is a cross-sectional image of an electrical feedthrough.

FIG. 1 is an abstract, cross-sectional drawing of feedthrough 10. Wire or pin 12 extends through ferrule 14. In various embodiments, electrically conductive pin 12 is comprised of a biocompatible metal, such as titanium, niobium or other metal, including precious metals. Insulative assembly 16 has an insulative assembly liquidus temperature, or melting temperature, and includes insulator 17 and provides at least partial physical insulation between first side 18 and second side 20 of feedthrough 10. Capacitor 22 provides some protection against certain changes in environmental electromagnetic conditions, including electromagnetic fields generated by external sources.

Preforms 24, 26, 28, 30 have a preform liquidus temperature and are, in various embodiments, comprised of gold. In an embodiment, the gold of preforms 24, 26, 28, 30 is substantially gold. In an embodiment, the gold of preforms 24, 26, 28, 30 is 99.99 percent (99.99%) gold as defined by ASTM B562. Preforms 24, 26, 28, 30 may be positioned with respect to pin 12, ferrule 14, insulator 17 and capacitor 22 to physically secure such components with respect to one another upon preforms 24, 26, 28, 30 having been heated at least to the preform liquidus temperature. First preforms 24, 26 may be positioned proximate or abutting first side 31 of capacitor 22, with first inner preform 24 being proximate pin 12 and first outer preform 26 being proximate ferrule 14. Second preforms 28, 30 are also included as part of insulative assembly 16 and further provide at least partial physical isolation between first side 18 and second side 20, with second inner preform 28 being proximate pin 12 and second outer preform 30 being proximate ferrule 14.

In various embodiments, ferrule 14 is comprised primarily of titanium, niobium, or alloys containing either titanium or niobium, or both. It is to be recognized and understood that, in certain embodiments, that other materials or other materials in addition to titanium and niobium, now existing or in the future developed, could be utilized.

In various embodiments, insulator 17 is comprised of either single crystal or polycrystalline materials based on alumina. In certain embodiments, insulator 17 is a ceramic material. Preforms 28, 30 in combination with pin 12 and insulator 17 function to impede most or all fluid and gas flow through ferrule lumen 32 of ferrule 14. By creating a seal extending the width of ferrule lumen 32, fluid and gas molecules which may pass through ferrule lumen 32 are substantially impeded.

In various alternative embodiments, insulative assembly 16 is comprised of a glass seal or other ceramic material having the insulative assembly liquidus temperature. In such embodiments, the glass seal may be configured to wet out or bond with pin 12 and ferrule 14. As a consequence, embodiments in which insulative assembly 16 incorporates a glass seal instead of insulator 17 may not incorporate preforms 28, 30.

In order to provide a seal, preforms 24, 26, 28, 30 are heated during manufacturing at least to the preform liquidus temperature. In embodiments in which preforms 24, 26, 28, 30 are gold, the preform liquidus temperature may be the liquidus temperature of gold, approximately one thousand sixty-three (1063) degrees Celsius). In various embodiments, feedthrough 10 is heated to approximately one thousand seventy-five (1075) degrees Celsius). In an embodiment, feedthrough 10 is heated to one thousand one hundred (1100) degrees Celsius). Upon being heated to the melting or liquidus temperature of preforms 24, 26, 28, 30, preforms 24, 26, 28, 30 soften or melt and flow, with molecules of preforms 24, 26, 28, 30 potentially chemically bonding to other adjacent molecules.

However, gold may not bond readily with all types of molecules. In particular, ceramic substances may not necessarily provide ready bonding with gold. In various embodiments, capacitor 22 is a barium titanate based capacitor, which is a ceramic material. In various embodiments, as noted above, insulator 17 is made of ceramic materials. In order to promote chemical bonding with the gold molecules of gold preforms 24, 26, 28, 30, inner and outer surfaces of insulator 17 and capacitor 22 may be treated with a metal coating having a coating liquidus temperature and which bonds readily with gold. Such treatment processes are known in the art as metallization, as noted above.

As further noted above, metallization of various components of feedthroughs, such as capacitor 22, has typically utilized silver-palladium. In an embodiment, both insulator 17 and capacitor 22 are metalized with a coating of niobium. Niobium has a coating liquidus temperature of at least up to one thousand one hundred (1100) degrees Fahrenheit (five hundred ninety-three (593) degrees Celsius). In alternative embodiments, insulator 17 and capacitor 22 are metalized with other metals which are thermally stable to temperatures at least as high as is necessary to melt gold and which may promote bonding with gold or whatever material comprises preforms 24, 26, 28, 30.

As a result of the various characteristics of insulative assembly 16, capacitor 22 and preforms 24, 26, 28, 30, feedthrough 10 may be manufactured by applying a temperature as described above which is higher than the insulative assembly liquidus temperature and the preform liquidus temperature, but not higher than the coating liquidus temperature. In the embodiment of FIG. 1, the insulative assembly liquidus temperature is equal to that of the preform liquidus temperature, as preforms 28, 30 of insulative assembly 16 have the lowest liquidus temperature of insulative assembly. In embodiments in which insulative assembly 16 incorporates a glass seal instead of insulator 17 and preforms 28, 30, the insulative assembly liquidus temperature may be the liquidus temperature of the glass seal. In any event, the temperature to which feedthrough 10 may be heated may still be defined as greater than the insulative assembly liquidus temperature and the preform liquidus temperature but less than the coating liquidus temperature.

Ferrule 14 forms hole 34 configured to provide access to gap 36 between insulative assembly 16 and second side 35 of capacitor 22. Owing to gap 36, surface arcing may tend occur between insulative assembly 16 and capacitor 22 in high voltage environments such as those caused by cardioversion or defibrillation shocks. In order to reduce a likelihood of such surface arcing, a non-conductive material 38 may be inserted or backfilled into gap 36 by way of hole 34. Non-conductive material 38 may fill or substantially fill gap 36. Such non-conductive material 38 may include polyimide, ethylene tetrafluoroethylene (or "ETFE"), a non-conductive epoxy and silicone. Hole 34 may also be utilized to determine a degree of seal provided by insulative assembly 16, such as during manufacturing testing.

In various alternative embodiments, gap 36 does not exist. Rather in such embodiments, insulative assembly 16 directly abuts second side 35 of capacitor 22. In certain such embodiments, insulative assembly 16 and capacitor 22 provide no gap 36 at all, in part to substantially avoid high voltage surface arcing. In various such embodiments, insulator 17 is a ceramic material such as a glass or glass-ceramic which is configured to bond with second side 35 of capacitor 22. In certain embodiments, second side 35 of capacitor 22 is metalized to provide bonding with insulator 17. In various alternative embodiments, either preform 28 or an additional preform (not illustrated) is configured to bond between insulator 17 and second side 35 of capacitor 22 to eliminate gap 36. Additional methods of eliminating gap 36 are contemplated.

Figure 2:
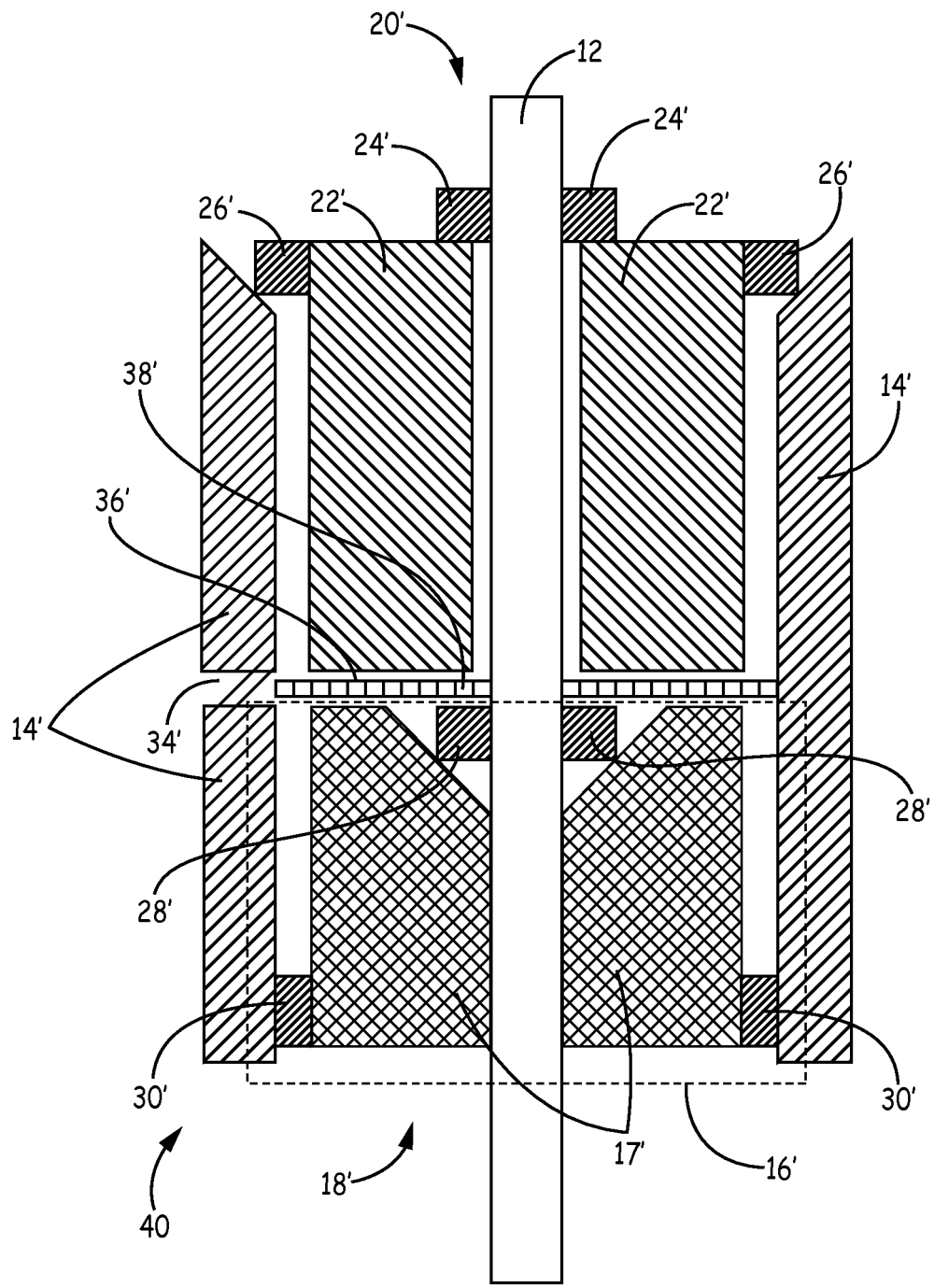
FIG. 2 is a cross-sectional image of an alternative electrical feedthrough.

FIG. 2 is an abstract, cross-sectional drawing of alternative feedthrough 40. Feedthrough 40 is related to feedthrough 10 in many respects, with most components being comprised of the same materials as related materials between feedthroughs 10, 40. Feedthrough 40 differs from feedthrough 10 in that ferrule 14' is substantially cylindrical, thereby potentially reducing a width of ferrule 14' and, as a consequence, feedthrough 40 in comparison with ferrule 14 and feedthrough 10, respectively.

Otherwise, while the components of feedthrough 40 may be independently selectable, and are not necessarily the same as corresponding components of feedthrough 10, in various embodiments, feedthrough 40 comprises components which are essentially the same as those of feedthrough 10. In various embodiments, insulative assembly 16' incorporates insulator 17' and preforms 28' and 30' made from the same materials as insulative assembly 16, insulator 17 and preforms 28 and 30 and thereby provide a seal between first side 18' and second side 20'. Capacitor 22' may be comprised of the same materials and metalized with a coating as with capacitor 22. Capacitor 22' may be secured with preforms 24' and 26' comprised of the same material as preforms 24, 26. Ferrule 14' may form hole 34' which may admit a non-conductive material 38' into gap 36'.

Figure 3:
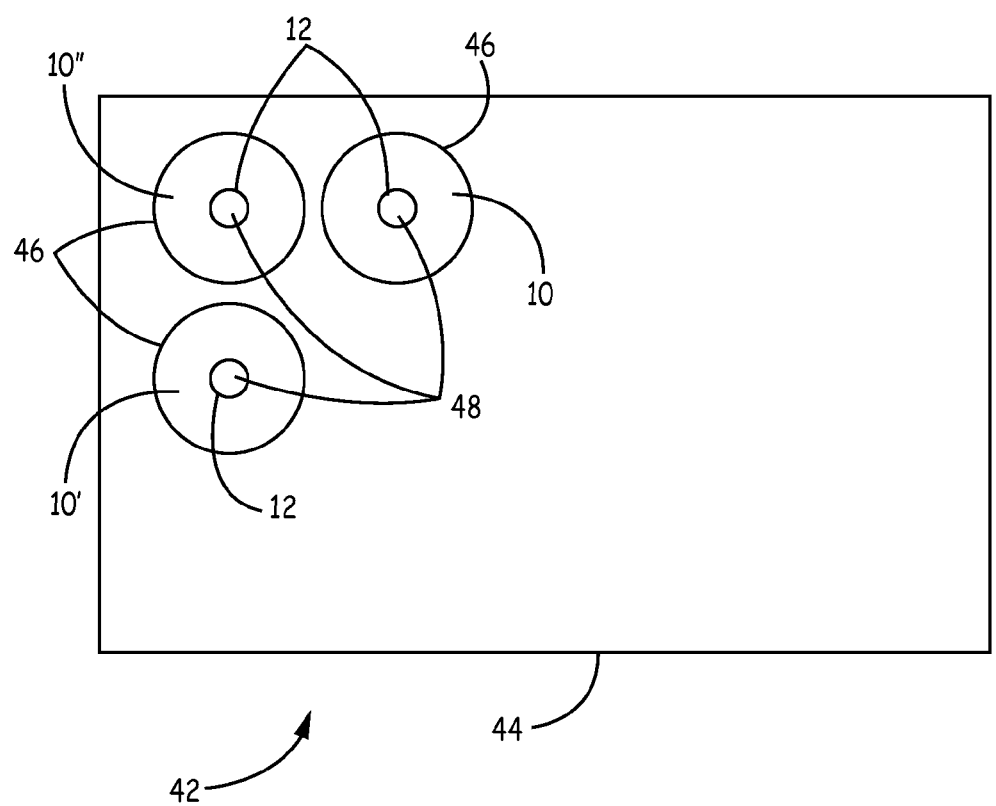
FIG. 3 is an abstract depiction of an implantable medical device incorporating multiple feedthroughs.

FIG. 3 is a diagrammatic illustration multiple feedthroughs 10 of an exemplary implantable medical device 42. In an alternative embodiment, implantable medical device 42 incorporates feedthroughs 40 (as illustrated in FIG. 2) either in place of or in addition to feedthroughs 10. In various embodiments, implantable medical device 42 has electronics for monitoring a patient condition and delivering an electrical therapeutic output. Such implantable medical devices 42 may include, but are not limited to, pacemakers, cardioverter/defibrillators and neurological stimulators. Implantable medical device 42 includes housing 44 enclosing certain electronics of implantable medical device 42. In various embodiments, housing 44 is substantially sealed for implantation in a patient. In an embodiment housing 44 is hermetically sealed. Feedthroughs 10 are positioned in feedthrough openings 46 and provide electrical connectivity between an object external to housing 44, such as a medical lead, and electronics of implantable medical device 42 contained within housing 44.

In various embodiments, centers 48 of pins 12 of adjacent feedthroughs 10 are separated by a predetermined distance. The predetermined distance may be minimized to promote housing 44 and implantable medical device 42 being relatively small. Advantageous use of the teachings herein may allow an implantable medical device having a plurality of feedthroughs 10 spaced more closely together than may otherwise have been realistically feasible. For example, an implantable medical device may be constructed with a plurality of feedthroughs 10 spaced at least as close to each other as being on fifty (50) mil (1.27 millimeters) centers. In such an embodiment, centers 48 of pins 12 of adjacent feedthroughs 10', 10" are separated by approximately fifty (50) mil (1.27 millimeters). In an exemplary embodiment incorporating feedthroughs 40 (as illustrated in FIG. 2), centers 48 of pins of adjacent feedthroughs 40 are separated by approximately thirty-five (35) mil (0.889 millimeters). In an example of use of such embodiments, feedthroughs 10, 40 may be configured to pass relatively low voltage current, such as may be utilized by a pacemaker or neurostimulator to deliver conventional stimulation pulses of generally less than 10 Volts in amplitude.

While relatively close center-to-center spacing of feedthroughs 10 may be desirable, it is also contemplated that in an embodiment, centers 48 of pins 12 of adjacent feedthroughs 10', 10" (or, alternatively, feedthrough 40, FIG. 2) may be separated by approximately fifty-five (55) mil (1.397 millimeters). In such embodiments, feedthroughs 10 may be configured to pass relatively high voltage current, such as may be utilized by a cardioverter/defibrillator to deliver conventional cardioversion/defibrillation pulses which have generally used spacings of greater than 70 mils (1.778 millimeters).

Figure 4:
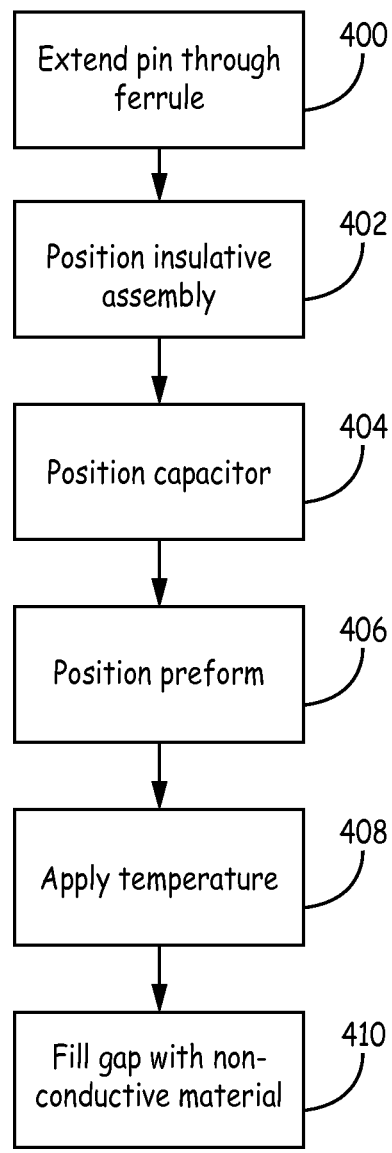
FIG. 4 is a flowchart for making a feedthrough.

FIG. 4 is a flowchart for making feedthrough 10 or 40. Pin 12 is extended (400) at least partially through ferrule 14.

Insulative assembly 16 is positioned (402) within ferrule 14 proximate second side 35 of capacitor 22. Capacitor 22 is positioned (404) within ferrule 14. First preforms 24, 26 are positioned (406) proximate first side 31 of capacitor 22 within ferrule 14. A temperature is applied (408) which is greater than the insulative assembly liquidus temperature and the preform liquidus temperature but less than the coating liquidus temperature of capacitor 22 so that at least pin 12, ferrule 14, insulative assembly 16, capacitor 22 and first preforms 24, 26 are secured with respect to one another. Gap 36 may be at least partially filled (410) with non-conductive material 38.

The invention claimed is:

1. An implantable medical device, comprising:
    a housing forming a plurality of feedthrough openings; and
    a plurality of feedthroughs, each individually positioned within one of said feedthrough openings, each feedthrough comprising:
    a ferrule made from a metal selected from the group consisting of titanium, niobium; an alloy of titanium; an alloy of niobium, and an alloy of titanium and niobium;
    an electrically conductive pin;
    a preform having a preform liquidus temperature;
    a capacitor, positioned within said ferrule abutting said preform, having a coating having a coating liquidus temperature and being configured to electrically couple with said preform; and
    an insulative assembly configured, at least in part, to seal against passage of a liquid through said ferrule, and having an insulative assembly liquidus temperature, wherein said insulative assembly and said capacitor form a gap within said ferrule between said insulative assembly and said capacitor, wherein said ferrule forms a hole proximate said gap and wherein said ferrule is configured so that non-conductive material may be inserted though said hole in said ferrule;
    said coating liquidus temperature being greater than said preform liquidus temperature; and
    said coating liquidus temperature being greater than said insulative assembly liquidus temperature.

2. The implantable medical device of claim 1 wherein said coating liquidus temperature, said preform liquidus temperature and said insulative assembly liquidus temperature are selected so that said preform, said capacitor, said insulative assembly, said pin and said ferrule are secured with respect to one another with a single step.

3. The implantable medical device of claim 2 wherein said single step comprises an application of heat.

4. The implantable medical device of claim 1:
    wherein said preform is a first preform comprised of a preform material;
    wherein said insulative assembly comprises an insulator and a second preform comprised of said preform material having said preform liquidus temperature and configured to secure said insulator with respect to said pin and said ferrule;
    wherein said insulative assembly liquidus temperature is equal to said preform liquidus temperature.

5. The implantable medical device of claim 4 wherein said first preform comprises a first inner preform proximate said pin and a first outer preform proximate said ferrule and said second preform comprises a second inner preform proximate said pin and a second outer preform proximate said ferrule.

6. The implantable medical device of claim 4 wherein said preform material is substantially gold and said preform liquidus temperature and said insulative assembly liquidus temperature are a liquidus temperature of gold.

7. The implantable medical device of claim 1 wherein said coating of said capacitor is comprised of niobium.

8. The implantable medical device of claim 1 wherein said gap is at least partially filled with a non-conductive material.

9. The implantable medical device of claim 1 wherein said pin extends longitudinally through said ferrule, said capacitor and said insulative assembly.

10. A feedthrough, comprising:
    a ferrule made from a metal selected from the group consisting of titanium, niobium; an alloy of titanium; an alloy of niobium, and an alloy of titanium and niobium;
    an electrically conductive pin;
    a preform having a preform liquidus temperature;
    a capacitor, positioned within said ferrule abutting said preform, having a coating having a coating liquidus temperature and being configured to electrically couple with said preform; and
    an insulative assembly configured, at least in part, to seal against passage of a liquid through said ferrule, and having an insulative assembly liquidus temperature, said insulative assembly and said capacitor form a gap within said ferrule between said insulative assembly and said capacitor, wherein said ferrule forms a hole proximate said gap and wherein said ferrule is configured so that non-conductive material may be inserted though said hole in said ferrule;
    said coating liquidus temperature being greater than said preform liquidus temperature; and
    said coating liquidus temperature being greater than said insulative assembly liquidus temperature.

11. The feedthrough of claim 10 wherein said coating liquidus temperature, said preform liquidus temperature and said insulative assembly liquidus temperature are selected so that said preform, said capacitor, said insulative assembly, said pin and said ferrule are secured with respect to one another with a single step.

12. The feedthrough of claim 11 wherein said single step comprises an application of heat.

13. The feedthrough of claim 10:
    wherein said preform is a first preform comprised of a preform material;
    wherein said insulative assembly comprises an insulator and a second preform comprised of said preform material having said preform liquidus temperature and configured to secure said insulator with respect to said pin and said ferrule;
    wherein said insulative assembly liquidus temperature is equal to said preform liquidus temperature.

14. The feedthrough of claim 13 wherein said first preform comprises a first inner preform proximate said pin and a first outer preform proximate said ferrule and said second preform comprises a second inner preform proximate said pin and a second outer preform proximate said ferrule.

15. The feedthrough of claim 13 wherein said preform material is substantially gold and said preform liquidus temperature and said insulative assembly liquidus temperature are a liquidus temperature of gold.

16. The feedthrough of claim 10 wherein said gap is at least partially filled with a non-conductive material.

* * * * *